(12) United States Patent
Brook et al.

(10) Patent No.: US 11,710,570 B2
(45) Date of Patent: *Jul. 25, 2023

(54) SYSTEMS AND METHODS FOR DETERMINING A RISK SCORE USING MACHINE LEARNING BASED AT LEAST IN PART UPON COLLECTED SENSOR DATA

(71) Applicant: BlueOwl, LLC, San Francisco, CA (US)

(72) Inventors: Callum Brook, Piedmont, CA (US); Kenneth Jason Sanchez, San Francisco, CA (US); Theobolt N. Leung, San Francisco, CA (US)

(73) Assignee: BlueOwl, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/670,041

(22) Filed: Feb. 11, 2022

(65) Prior Publication Data

US 2022/0165429 A1    May 26, 2022

Related U.S. Application Data

(63) Continuation of application No. 16/798,869, filed on Feb. 24, 2020, now Pat. No. 11,276,501.

(51) Int. Cl.
*G16H 50/30* (2018.01)
*G16H 50/20* (2018.01)
(Continued)

(52) U.S. Cl.
CPC ........... *G16H 50/30* (2018.01); *G06F 18/214* (2023.01); *G06Q 40/08* (2013.01); *G16H 20/00* (2018.01); *G16H 50/20* (2018.01)

(58) Field of Classification Search
CPC ........ G16H 50/30; G16H 50/20; G16H 20/00; G06F 18/214; G06Q 40/08
(Continued)

(56) References Cited

U.S. PATENT DOCUMENTS 8,515,777 B1 *   8/2013  Rajasenan ............. G16H 50/30
                                                            705/7.14
8,849,610 B2     9/2014  Molettiere et al.
(Continued)

FOREIGN PATENT DOCUMENTS

CN            202282004 U     6/2012

OTHER PUBLICATIONS

Kantoch, Recognition of Sedentary Behavior by Machine Learning Analysis of Wearable Sensors during Activities of Daily Living for Telemedical Assessment of Cardiovascular Risk, Sep. 24, 2018, Sensor Applications In Medical Monitoring and Assistive Devices 18(10), 3219, https://doi.org/10.3390/s1 (Year: 2018).*
(Continued)

*Primary Examiner* — Joy Chng
(74) *Attorney, Agent, or Firm* — Faegre Drinker Biddle & Reath LLP

(57) ABSTRACT

A system and method for analyzing risk and providing risk mitigation instructions. The system receives analyzes sensor data and other data corresponding to a user to determine a test group. The system uses the test group to determine a risk score, and, subsequently, a risk mitigation strategy. Machine learning techniques are implemented to refine how the test group, risk score, and mitigation are each selected.

20 Claims, 7 Drawing Sheets

(51) Int. Cl.
*G16H 20/00* (2018.01)
*G06Q 40/08* (2012.01)
*G06F 18/214* (2023.01)

(58) Field of Classification Search
USPC .......................................................... 705/2–3
See application file for complete search history.

(56) References Cited

U.S. PATENT DOCUMENTS

| | | |
|---|---|---|
| 9,398,854 B2 | 7/2016 | Proud |
| 9,418,383 B1 | 8/2016 | Hayward et al. |
| 10,068,673 B2 | 9/2018 | Madan et al. |
| 10,157,267 B2 | 12/2018 | Mitchley |
| 10,581,896 B2 * | 3/2020 | Nachenberg ............ G06F 21/50 |
| 2016/0373477 A1 * | 12/2016 | Moyle ................. H04L 63/1433 |
| 2017/0220751 A1 * | 8/2017 | Davis ...................... G16H 40/63 |
| 2017/0286621 A1 * | 10/2017 | Cox ........................ G16H 50/20 |
| 2019/0251456 A1 * | 8/2019 | Constantin ........... A61B 5/7282 |

OTHER PUBLICATIONS

Robben et al., Delta Features From Ambient Sensor Data are Good Predictors of Change in Functional Health, IEEE Journal of Biomedical and Health Informatics, vol. 21, No. 4, pp. 986-993, Jul. 2017, doi: 10.1109/JBHI.2016.2593980 (Year: 2017).*

Vandendooren, T. & Dingemanse, T. (Feb. 2017). RISK: From usage to user based insurance. Sentiance. Retrieved from https://www.sentiance.com/2017/02/27/ubi-user-based-insurance/.

* cited by examiner

SYSTEMS AND METHODS FOR DETERMINING A RISK SCORE USING MACHINE LEARNING BASED AT LEAST IN PART UPON COLLECTED SENSOR DATA

This application is a continuation of U.S. patent application Ser. No. 16/798,869, filed Feb. 24, 2020, which is incorporated by reference herein for all purposes.

TECHNICAL FIELD

The present disclosure relates to systems and methods for determining risk scores for users, such as using machine learning techniques to analyze user related data to enhance the accuracy of the risk scores and to develop risk mitigation strategies.

BACKGROUND

Although it can be difficult to measure risk accurately, assessing a person's risk level is important and can be valuable in various applications such as accurately pricing insurance for the person and/or providing risk mitigation strategies to the person to help them improve their health and/or avoid accidents. Typical data used to determine a person's risk level include age, weight, occupation, smoking habits, drinking habits, etc. However, there may be additional data that can be used to more accurately assess a person's risk.

SUMMARY

One embodiment of the current disclosure provides a computer-implemented method for providing risk analysis and mitigation, the method includes receiving, by one or more processors, a request for risk analysis of a user and sensor data indicative of one or more physical measurements corresponding to the user. The method further includes retrieving, by one or more databases communicatively coupled to the one or more processors, demographic data corresponding to the user. The method also includes analyzing, by the one or more processors, the sensor data and the demographic data to determine a pattern of behavior of the user. The method further includes, selecting a test group corresponding to the user based at least in part upon the pattern of behavior, where the test group is one of a plurality of test groups, and wherein the test group includes a plurality of subjects each corresponding to the pattern of behavior of the user. The method also includes determining, by the one or more processors, a risk score of the user based at least in part upon the test group.

In another embodiment, the current disclosure provides a system for providing risk analysis and mitigation, the system comprising: a back-end server; and a risk module configured to execute on one or more processors, the risk module configured to execute at least partially on the back-end server, the risk module configured to receive a request for risk analysis of a user and sensor data indicative of one or more physical measurements corresponding to the user. The module further configured to retrieve, from one or more databases communicatively coupled to the back-end server, demographic data corresponding to the user. The module also configured to analyze the sensor data and the demographic data to determine a pattern of behavior of the user. The module further configured to select a test group corresponding to the user based at least in part upon the pattern of behavior, where the test group is one of a plurality of test groups, and wherein the test group includes a plurality of subjects each corresponding to the pattern of behavior of the user. The module configured to determine a risk score of the user based at least in part upon the test group.

In still another embodiment, the current disclosure provides a tangible computer-readable medium including non-transitory computer readable instructions stored thereon for providing risk analysis and mitigation, the instructions to implement a risk module configured to execute on one or more processors, the risk module configured to receive a request for risk analysis of a user and sensor data indicative of one or more physical measurements corresponding to the user. The module further configured to retrieve, from one or more databases communicatively coupled to the back-end server, demographic data corresponding to the user. The module also configured to analyze the sensor data and the demographic data to determine a pattern of behavior of the user. The module further configured to select a test group corresponding to the user based at least in part upon the pattern of behavior, where the test group is one of a plurality of test groups, and wherein the test group includes a plurality of subjects each corresponding to the pattern of behavior of the user. The module configured to determine a risk score of the user based at least in part upon the test group.

Depending upon the embodiment, one or more benefits may be achieved. These benefits and various additional objects, features and advantages of the present disclosure can be fully appreciated with reference to the detailed description and accompanying drawings that follow.

DETAILED DESCRIPTION

The system of this disclosure implements one or several techniques discussed below for determining risk scores for users and generating risk mitigation strategies. Rather than simply relying on typical demographic data (e.g., age, height, weight, occupation) to assess a user's risk, the current disclosure implements a number of sensors to collect data to be used in determining a risk score, and a number of machine learning algorithms to analyze the collected sensor data. The sensors include accelerometers, gyroscopes, GPS, and heart rate monitors, which are housed in devices associated with the user. The data collected from the sensors is analyzed through a machine learning algorithm to identify a test group which corresponds to the activity pattern of the user. Next, a risk score is calculated based at least in part upon the test group. The risk score is then used to identify a risk mitigation strategy, which is also refined through an iterative machine learning process. The entire process may be improved as more data is collected and results are assessed.

Figure 1A:
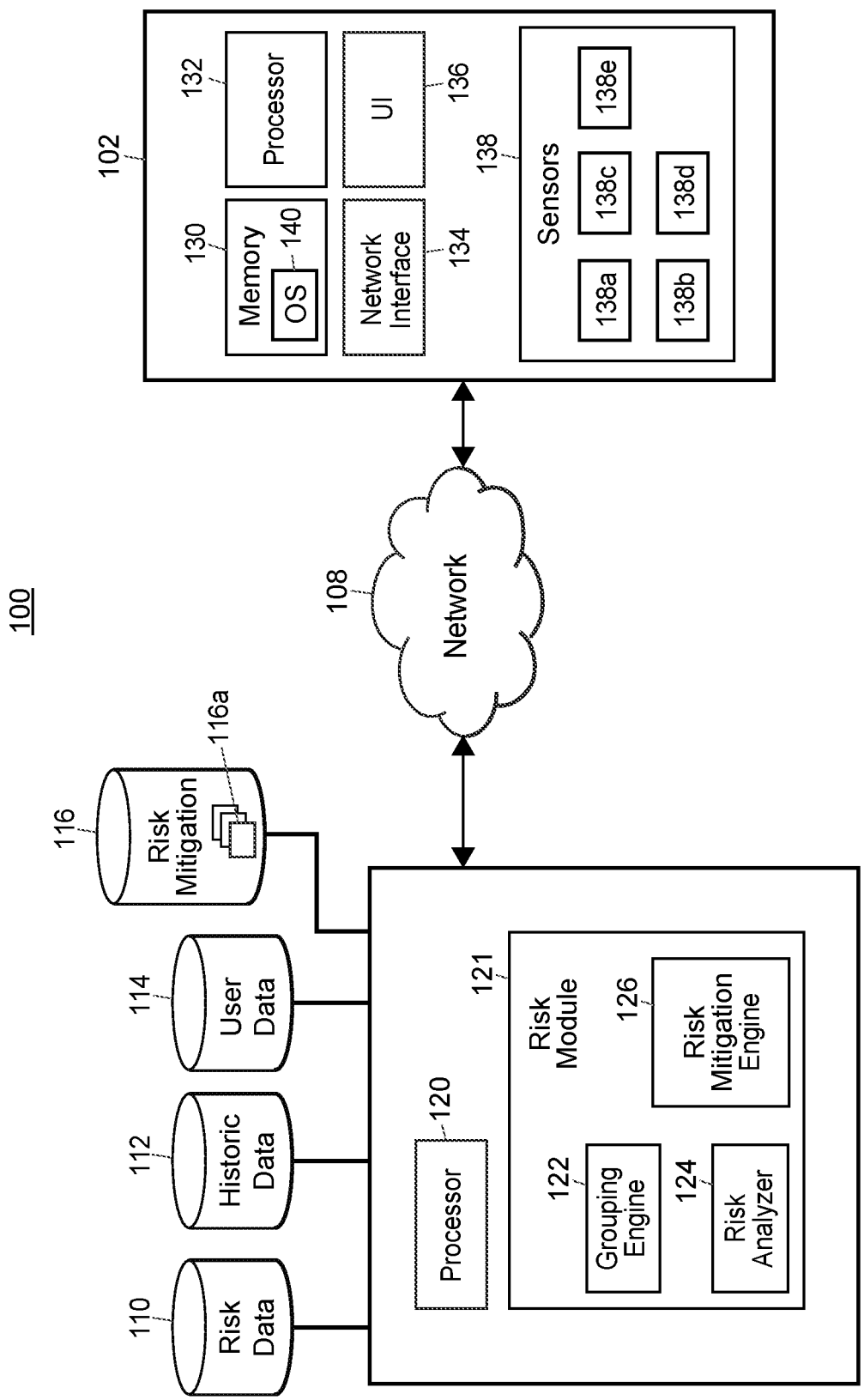
FIG. 1A is a block diagram of an example system in which techniques for determining risk scores can be implemented.
Figure 1B:
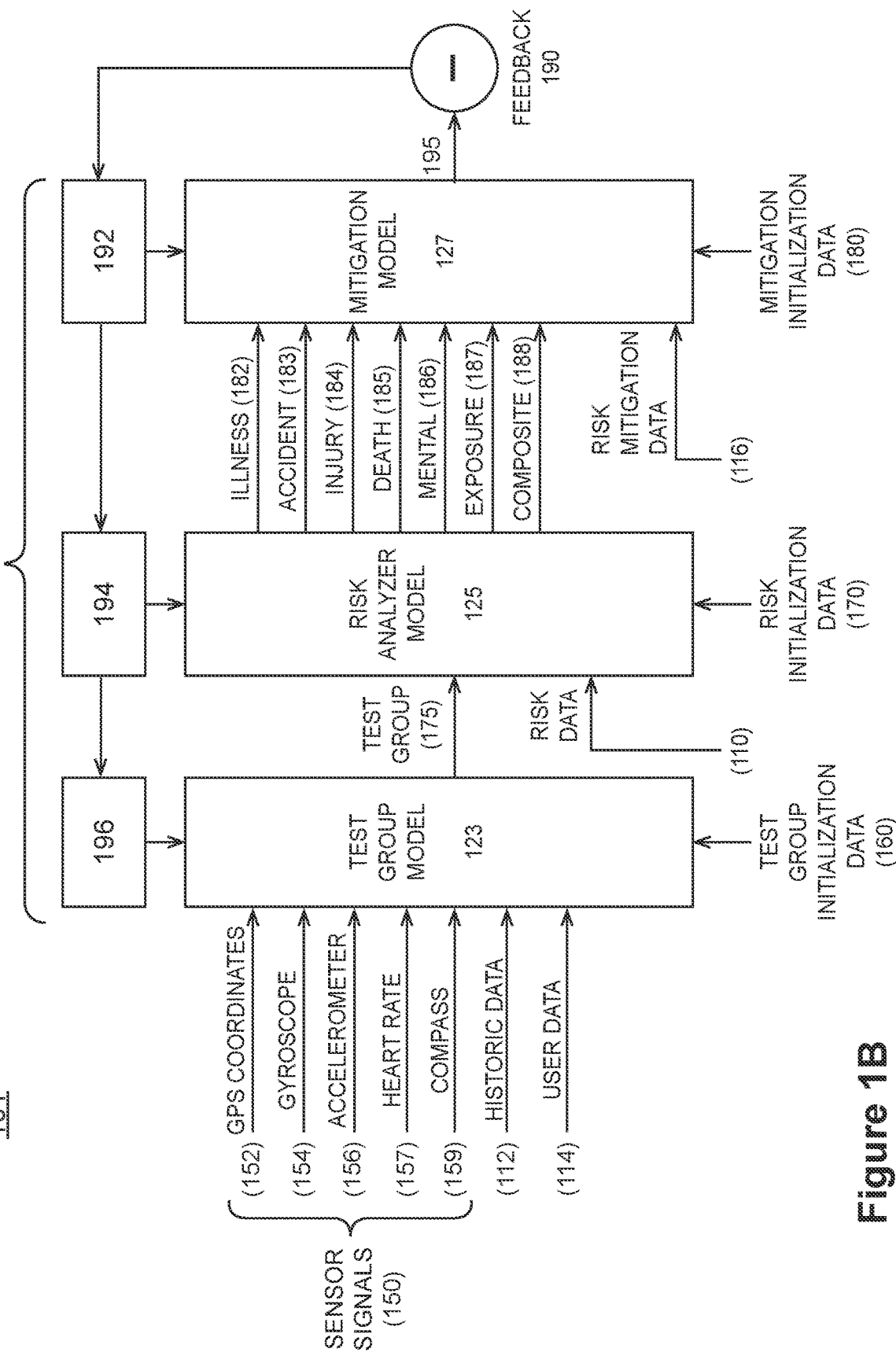
FIG. 1B is a block diagram of an example machine learning model which the system of FIG. 1A can use to determine risk scores.

FIG. 1A is a block diagram of an example system in which techniques for determining risk scores can be implemented. FIG. 1B is a block diagram of an example machine learning model which the system of FIG. 1A can use to determine risk scores. An example computing environment in which the system of this disclosure can operate is discussed first with reference to FIG. 1A and FIG. 1B, followed by a discussion of several example use cases with reference to FIG. 2 and FIG. 3, and further followed by a discussion of several example methods that can be implemented in the system of FIG. 1.

Referring to FIG. 1A, an example computing environment 100 in which the techniques outlined above can be implemented includes an example client computing device 102 which can be, for example, a personal computer, a portable device such as a tablet computer or smartphone, wearable computing device such as a smartwatch, a special-purpose car navigator, a device embedded in a head unit of a vehicle, etc. The computing environment 100 in general can include any suitable number of client computing devices.

The computing environment 100 further includes one or more servers 104 operated by a provider of risk analysis, such as an insurance company. The server 104 can receive data from the client computing device 102 and other client devices. The computing environment 100 in general can include any suitable number of providers of content and/or databases related to risk analysis including risk data, customer information, historic risk analysis, etc. The server 104 and the client computing device 102 can communicate via a network 108, which can be a wide area network such as the internet, for example, and include wired and/or wireless communication links.

The server 104 can be communicatively coupled to a database 110 that stores risk data. The risk data can include various data related to risk analysis including insurance products such as claims, products, rates, etc. The risk data can include data relating to insurance product such as auto insurance, home insurance, personal liability, etc. The risk data can also include actuarial data and other data that typically informs how risk is calculated, such as weather data, map data, accident data, etc. Further, risk data can include risk profiles for certain activities, professions, areas, etc.

The server 104 also is coupled to a historic database 112 which stores anonymized sensor data for multiple users, each of which can be made up of position/time tuples, for example. In some implementations, users operate certain controls and/or install certain applications to indicate that the server 104 may use their sensor data to determine risk scores and develop risk mitigation strategies. As indicated above, the sensor data may be collected from one or more sensors installed in one or more devices, such as client device 102. Sensors data may include position data, accelerometer data, heart rate data, gyroscope data, etc. The sensor data may be correlated to other data, such as user data from database 114 in order to allow the system to identify test groups of users.

The server 104 may also be communicatively coupled to a user database 114 that stores demographic data for users operating client devices such as the device 102. Similar to the example above, users can operate certain controls and/or install certain applications to indicate that the server 104 can use their demographic data to determine risk scores and develop risk mitigation strategies. As one example, user-specific data in the database 114 can indicate a user's age, weight, income bracket, etc., all components which have been previously used in known systems to analyze risk.

Additionally, the server may be communicatively coupled to a risk mitigation database 116 that stores data related to risk mitigation. For example, the risk mitigation database 116 may store a series of communications 116a that can be sent to a user in response to a risk score. For example, if a user has a risk score that indicates a high risk of injury, the risk mitigation strategy may send a communication 116a as a notification to a user's phone indicating that the user should take a short walk, with similar notifications sent to the user throughout the day. In another example, if the system determines that a user is at risk for heart disease, the risk mitigation data base 116 may include a series of communications 116a detailing workouts that the user can perform to lower their risk. The communications 116a can be sent as videos to a client device corresponding to the user, such as client device 102. The types of communications 116a stored in the risk mitigation database 116 are discussed in greater detail with respect to FIG. 3, below.

In general, the server 104 can access any suitable number of databases not pictured in FIG. 1A, such as those storing insurance claims, insurance pricing algorithms, risk determination algorithms, traffic data, weather data, crime data, etc.

With continued reference to FIG. 1A, the server 104 includes one or more processors 120 and a non-transitory memory (e.g., a hard disk, a flash drive) storing instructions that implement a risk analysis system including a risk module 121 including a grouping engine 122, a risk analyzer 124, and a risk mitigation engine 126. The instructions that implement the modules 121, 122, 124, and 126 are executable on the one or more processors 120.

The risk module 121 can implement any of the modules 122, 124, and 126 to determine risk scores and identify risk mitigation strategies. The risk module 121 can ensure that sensor data and other data (such as data from databases 110, 112, 114, and 116) are authorized and can be used by modules 122, 124, and 126. Further, the risk module 121 can receive and collect data for use by the modules 122, 124, and 126. The risk module 121 may also collect and transmit and outputs from grouping engine 122, risk analyzer 124, and risk mitigation engine 126.

In an example embodiment, using the data stored in the databases 110, 112, 114, 116, including any additional data stored at a publicly accessible database, a grouping engine 122 can identify a number of test groups including individuals that exhibit similar patterns of behavior. In another embodiment, the grouping engine 122 can additionally receive sensor data from one or more client devices, such as the device 102, associated with a particular user to determine a test group for the particular user. The grouping engine can identify a pattern of behavior based at least in part upon the collected sensor data and subsequently identify a test group related to the user's pattern of behavior. The grouping engine 122 is discussed in greater detail below with respect to FIG. 1B.

The risk analyzer 124 then analyzes the profile of the test group and generates a risk score for the test group. The risk score can include a score for various types of risk including risk of: death, injury, illness, accident, exposure, mental health issues, etc. Additionally, the risk score may also include an aggregate risk score analyzing the user's overall risk level. The risk analyzer 124 is discussed in greater detail below with respect to FIG. 1B and FIG. 2.

The risk mitigation engine 126 can determine a risk mitigation strategy based at least in part upon the risk score. The risk mitigation engine, in some implementations, heuristically uses various communications from the risk mitigation database 116, user-specific data from such sources as the database 114 and the client computing device 102, and the risk score determined by risk analyzer 124 to determine a risk mitigation strategy. As one example of determining a risk mitigation strategy heuristically, the risk mitigation database 116 can store a number of generic communications aimed at users with a high risk score, the risk mitigation engine 126 can select a number of the generic communications for every user with a risk score above a threshold. In other implementations, the risk mitigation engine 126 uses machine learning techniques to select a risk mitigation strategy from the communications 116a, as discussed with reference to FIG. 1B.

With continued reference to FIG. 1A, the client computing device 102 can include a memory 130, one or more processors 132, a network interface 134, a user interface (UI) 136, and sensors 138. The memory 130 can be a non-transitory memory and can include one or several suitable memory modules, such as random-access memory (RAM), read-only memory (ROM), flash memory, other types of persistent memory, etc. The network interface 134 can support any suitable communication protocol to communicate with remote servers and other devices via the communication network 108. The UI 136 can include any suitable combination of input devices such as a touchscreen, a keyboard, a microphone, etc. and output devices such as screens, speakers, etc. The memory 130 stores an operating system (OS) 140, which can be any type of suitable mobile or general-purpose operating system.

Depending on the implementation, the one or more sensors 138 can include a global positioning system (GPS) module 138a to detect the position of the client computing device 102, a compass 138b to determine the direction of the client computing device 102, a gyroscope 138c to determine the rotation and tilt, an accelerometer 138d to determine the speed and movement of the device, a heart rate monitor 138e to measure the heart rate of a user associated with the device, etc. The sensors data from the sensors 138 can be provided to the server 104 periodically or continuously, depending on the implementation. Further, the sensor data from sensors 138 may be stored in a database such as historic database 112 or in the user database 114.

For simplicity, FIG. 1A illustrates the server 104 as only one instance of a server device. However, the server 104 according to some implementations includes a group of one or more server devices, each equipped with one or more processors and capable of operating independently of the other server devices. Server devices operating in such a group can process requests from the client computing device 102 individually (e.g., based at least in part upon availability), in a distributed manner where one operation associated with processing a request is performed on one server device while another operation associated with processing the same request is performed on another server device, or according to any other suitable technique. For the purposes of this discussion, the term "server" may refer to an individual server device or to a group of two or more server devices.

Now referring to FIG. 1B, which illustrates a machine learning model 101 for determining risk scores and identifying risk mitigation strategies. The machine learning model 101, may be implemented by, for example, risk module 121 of FIG. 1A, including the corresponding grouping engine 122, risk analyzer 124, and risk mitigation engine 126. The machine learning model 101 is intended to be an iterative model that improves as larger data sets and feedback (190) are received and the models (123, 125, 127) are refined through adjustments (192, 194, 196).

The grouping engine 122, in some implementations, trains a test group machine learning model ("test group model") 123 using various inputs, retrieved data, test group initialization data 160, feedback 190, etc. The grouping engine 122 can receive various inputs 152, 154, 156, 157, 159, 114, and 112, as training data and apply the training data to the test initialization data 160 to train the test group model 123. The test group initialization data 160 may provide a preselected number of test groups 175 related to various categories.

As larger sets of data are received, the grouping engine 122 can further refine test group model 123 to refine the test groups 175 and improve results. For example, as more sensor signals 150 are received, the test group model 123 can more specifically cluster data from the sensor signals 150 to identify patterns of behavior, and subsequently identify test groups 175 that are more specifically tailored and contain a relevant group of users. Further, the grouping engine 122 can receive feedback 190, when available, to assess the quality of the test groups 175 and continue tuning the test group model 123. To this end, an adjustment function 196 can receive a metric assessing the difference between the actual and expected outputs of the test group model 123, generate adjustment operations, and apply these operations to the test group model 123. For example, the feedback 190 may include data indicative of the number of accidents, deaths, insurance claims, etc. from members within the test group. The grouping engine 122 can then evaluate the feedback 190 to determine if the users in the test group were accurately grouped together and, if not, how to adjust the test group model 123 to reflect the feedback 190.

The grouping engine 122 uses a number of sensor signals 150 to help train the test group model 123. The sensor signals 150 may be received from sensors such as sensors 138 of client device 102 in FIG. 1A. The sensor signals 150 may include GPS coordinates 152, gyroscope signals 154, accelerometer signals 156, heart rate signals 157, and compass signals 159. The grouping engine 122 analyzes along with user data 114, and historic data 112 in order to identify patterns of behavior, which can then inform the selection of test groups 175.

The test groups 175 are intended to identify groups of users with similar patterns of behavior. Unlike previous risk analysis systems which identify users by simple metrics such as age, height, weight, and occupation, the current system is aimed at grouping users by where and how users spend their time throughout their day and using these patterns of behavior to identify risk factors. For example, a user's location (e.g., provided by GPS signals 152) factors into their risk score. However, while two separate users may both spend eight hours at work and 12 hours at home throughout a typical day, the users might accumulate those hours differently. The first user may arrive at their workplace and then spend eight hours at work consecutively, while the second user may spend eight total hours at the workplace but leave every few hours to spend time at other locations. In this example, while both users spend the same total amount of time in the workplace, their risk profile may vary greatly. The first user may have a lower risk of accident, but have a higher health risk due to a more sedentary lifestyle. The second user may be at greater risk for injury and/or accidents, but have less of a mental health risk because they spend more time outside.

Further, while GPS signals 152 may provide insight into where a user spends their time, the other sensor signals 150 may provide insight into how the user spends time at those places. As mentioned above, using basic metrics, such as occupation, to analyze risk is well developed. However, the current system looks at how a user spends time at work (and other locations) by analyzing sensor signals 150. The test group model 123 may analyze the sensor signals 150 to determine how engaged is user is at their occupation (and other locations).

For example, construction workers are typically considered to have a higher risk of injury/accident compared to people in other professions and current systems generally analyze all constructions workers as having a high liability for risk. To prevent blanket assumptions, which may not be accurate for all people in the same professions, the current system may further analyze sensor signals 150 to determine how each construction worker spends their time within the work place. In an example, some construction workers may have higher heart rates while working than others. Through machine learning using an iterative process applying feedback, as described below, the system may determine that there is a correlation between the workers that have higher heart rates and injuries at the workplace.

In the above example, all construction workers would not simply be lumped into one group for risk analysis purposes. Instead, the construction workers with a higher heart rate in the work place may be grouped together while construction workers with lower heart rates may be grouped together. Further, either of the above groups may include users that are not construction workers, but otherwise have similar patterns of behavior. Further still, construction workers can be further broken into smaller test groups based at least in part upon patterns in their behavior, such as number of hours worked per day, the time of the day when they work (e.g., morning or evening), how they spend their time outside of the workplace (e.g., at the gym compared to at bars/restaurants), they types of locations they work, the types of activities they perform in the workplace (e.g., supervising as opposed to physical labor), etc. In this manner, the system may be able to better analyze each individuals risk profile instead of generalizing simply based at least in part upon a few demographic factors such as occupation.

In other words, while test groups may comprise a number of users that have similar occupations, the test groups do not necessarily have to be narrowed down based at least in part upon specific demographic details. Instead, the test group model 123 analyzes the sensor signals 150 to determine patterns of behavior which are used to identify test groups 175, where the patterns of behavior are correlated to certain types of risk. The test group model 123 may use many factors for determining patterns of behavior such as time at home, time at work, time driving, time at the gym, time eating, time spent at each location, time of day when at each location, the frequency of visits to each location, driving routes, driving speeds, which can be inferred from the sensor signals 150.

Next, the risk analyzer 124, in some implementations, trains a risk analyzer machine learning model ("risk analyzer model") 125 using various inputs, retrieved data, feedback 190, etc. The risk analyzer 124 can receive various inputs 175 and 110, as training data and apply this data to the risk initialization data 170 to train the risk analyzer model 125. The risk initialization data 170 may include a preselected set of algorithms for determining risk scores for test groups based at least in part upon a number of factors.

As larger sets of data are received, the risk analyzer 124 can further refine the risk analyzer model 125 to further refine the risk scores 182, 183, 184, 185, 186, 187, and 188 and improve results. For example, as more refined test groups 175 are received, the risk analyzer model 125 can determine more accurate risk scores 182, 183, 184, 185, 186, 187, and 188. Further, the risk analyzer 124 can receive feedback 190, when available, to assess the quality of the risk scores 182, 183, 184, 185, 186, 187, and 188 and continue tuning the risk analyzer model 125. To this end, an adjustment function 194 can receive a metric assessing the difference between the actual and expected outputs of the risk analyzer model 125, generate adjustment operations, and apply these operations to the risk analyzer model 125. For example, the feedback 190 may include data indicative of the number of accidents, deaths, insurance claims, etc. from members within the test group. The risk analyzer 124 can then evaluate the feedback 190 to determine if the risk scores 182, 183, 184, 185, 186, 187, and 188 for the test group were accurate and, if not, how to adjust the risk analyzer model 125 to reflect the feedback 190.

The risk analyzer model 125 may return a number of different risk scores 182, 183, 184, 185, 186, 187, and 188. In an embodiment, the risk analyzer model 125 may determine a risk score for any of the following risks: illness 182, accident 183, injury 184, death 185, mental health risk 186, exposure risk 187, and an overall composite risk score 188. Each of the risk scores 182, 183, 184, 185, 186, 187, and 188 is described in greater detail below with respect to FIG. 2.

Next, the risk mitigation engine 126, in some implementations, trains a mitigation machine learning model ("mitigation model") 127 using various inputs, retrieved data, feedback 190, etc. The risk mitigation engine 126 can receive various inputs such as risk scores 182, 183, 184, 185, 186, 187, and 188 and risk mitigation data 116, as training data and apply this data to the mitigation initialization data 180 to train the mitigation model 127. The mitigation initialization data 180 may include a preselected set of communications based at least in part upon generic ranges of risk scores.

As larger sets of data are received, the risk mitigation engine 126 can further refine the mitigation model 127 refine the risk mitigation strategies 195 and improve results. For example, as more risk scores 182, 183, 184, 185, 186, 187, and 188 are received, the mitigation model 127 can determine more accurate risk scores 182, 183, 184, 185, 186, 187, and 188. Further, the risk mitigation engine 126 can receive feedback 190, when available, to assess the quality of the risk mitigation strategies 195 and continue tuning the mitigation model 127 accordingly. To this end, an adjustment function 192 can receive a metric assessing the difference between the actual and expected outputs of the mitigation model 127, generate adjustment operations, and apply these operations to the mitigation model 127. For example, the feedback 190 may include data indicative of the number of accidents, deaths, insurance claims, etc. from members within the test group. The risk mitigation engine 126 can then evaluate the feedback 190 to determine if the number of incidents was better or worse than the expected incident rate based at least in part upon the risk scores. The risk mitigation engine 126 can then adjust the mitigation model 127 based at least in part upon the results by determining which communications were successful compared to other communications, and subsequently weighing the successful communications higher such that the successful communications will have a higher likelihood of being selected in further risk mitigation strategies 195.

The mitigation model 127 may return a risk mitigation strategy 195 comprised of a series of communications. In an embodiment, the mitigation model 127 may determine an overall risk mitigation strategy based at least in part upon any of the risk scores 182, 183, 184, 185, 186, 187, and 188, where the communications are meant to guide and/or encourage a user to implement behaviors that will lower their chance of having an accident and/or incident and/or to improve their overall health. The risk mitigation strategy 195 is described in greater detail below with respect to FIG. 3.

After the models 123, 125, and 127 are sufficiently trained (e.g., as discussed above, the tuning process can continue even after the models 123, 125, and 127 are sufficiently trained to continue improving the performance), the system can receive sensor data from one or more users to determine risk scores and provide risk mitigation strategies. In particular, a user can authorize a risk module to receive sensor data to determine a risk score. The risk module 121 may then collect sensor data continuously or periodically, depending on the embodiment, from one or more client devices corresponding to the user. Once sufficient sensor data is collected and other data retrieved from relevant databases (such as databases 110, 112, 114, and 116 of FIG. 1), the risk module may implement any of the grouping engine 122, risk analyzer 124, and risk mitigation engine 126 along with any of the corresponding models 123, 125, and 126 to determine risk scores 182, 183, 184, 185, 186, 187, and 188 and identify risk mitigation strategies 195.

Figure 2:
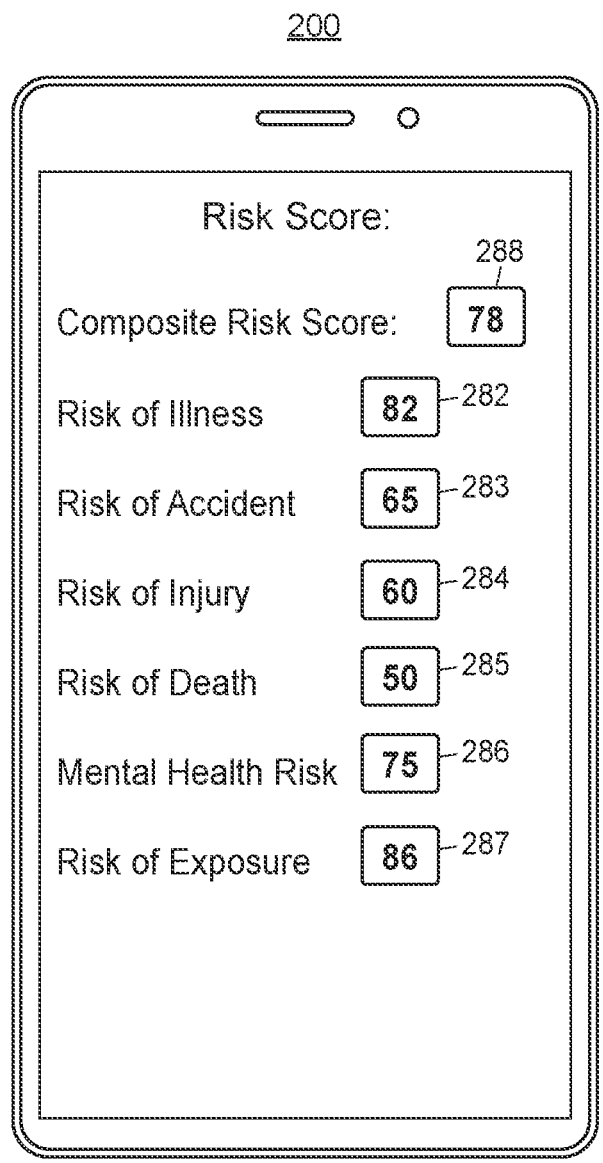
FIG. 2 is an example user interface screen displaying a risk score as determined by the system of FIG. 1A.

FIG. 2 illustrates an example user-interface 200 displaying a risk score, such as risk score 182, 183, 184, 185, 186, 187, and 188 determined by the risk analyzer model 125. In the example embodiment of FIG. 2, the risk scores 282, 283, 284, 285, 286, 287, and 288 are displayed numerically. However, the risk scores can be in any suitable form, such as a percentage, a percentile, a probability, a letter grade, etc. As described above, the risk scores 282, 283, 284, 285, 286, 287, and 288 are based at least in part upon the patterns of behavior of a test group, where the test group is analyzed as a representation of each of the users within the test group.

The risk scores 282, 283, 284, 285, 286, 287, and 288 are influenced to some degree by the sensor data used to identify test groups. For example, risk of illness 282 may depend on GPS data (e.g., as well as other data obtained from sensors). Similarly, the risk of exposure 287 may depend on GPS data. For example, if a user spends a lot of time outdoors then they might be at risk to damage from UV rays and other ailments related to exposure to the sun.

The risk of accident 283 may also depend on GPS data (e.g., as well as other data obtained from sensors). For example, the GPS data may indicate that the users of the test group spend a lot of time driving or that the users spend time driving on roads with a particularly high rate of vehicle collisions. This type of information may similarly indicate a high risk of injury 284. Other sensor data that might influence the risk of accident and/or risk of injury include accelerometer and gyroscope data. Accelerometer and gyroscope data may indicate that users perform quick and vigorous actions, such as run up and down stairs as opposed to walking, or that users perform intense aerobic activities. Conversely, accelerometer and gyroscope data may show that users have a relatively sedentary lifestyle, which may indicate a lower risk of accident 283 and/or injury 284, but a higher risk of illness 282.

In an embodiment, heart rate data may influence the determination of a risk score related to death 285 or mental health 286. For example, if users have a relatively high heart rate, that may indicate they have issues with heart health, which could contribute to a higher risk score for death 285. Similarly, a higher heart rate may indicate that users struggle with anxiety or other ailments, which may contribute to a higher risk for mental health 286.

The risk scores 282, 283, 284, 285, 286, 287, and 288 are generally represented by an overall composite risk score 288. The composite risk score 288 represents the overall likelihood of risk for a member of the test group. In some embodiments, the composite risk score 288 is an average of the other risk scores 282, 283, 284, 285, 286, and 287. In another embodiment, the composite risk score 288 indicates an overall risk score for an individual of the test group, and is calculated separately from the other risk scores 282, 283, 284, 285, 286, and 287 (though some of the same data used to calculate risk scores 282, 283, 284, 285, 286, and 287 may be used to calculate the composite risk score 288).

The above example risk scores 282, 283, 284, 285, 286, 287, and 288 are not intended to be limiting, any relevant risk score can be determined by the risk module 121 of FIG. 1A. The risk scores 282, 283, 284, 285, 286, 287, and 288 can be used to inform risk mitigation strategies, as discussed below with respect to FIG. 3. Further, the risk score 282, 283, 284, 285, 286, 287, and 288 may be used to inform insurance providers how to accurately price insurance policies. Similarly, the risk scores 282, 283, 284, 285, 286, 287, and 288 can be implemented by medical professionals in order to help treat patients and determine how patients can make changes in order to improve their quality of life and increase their lifespan.

Figure 3:
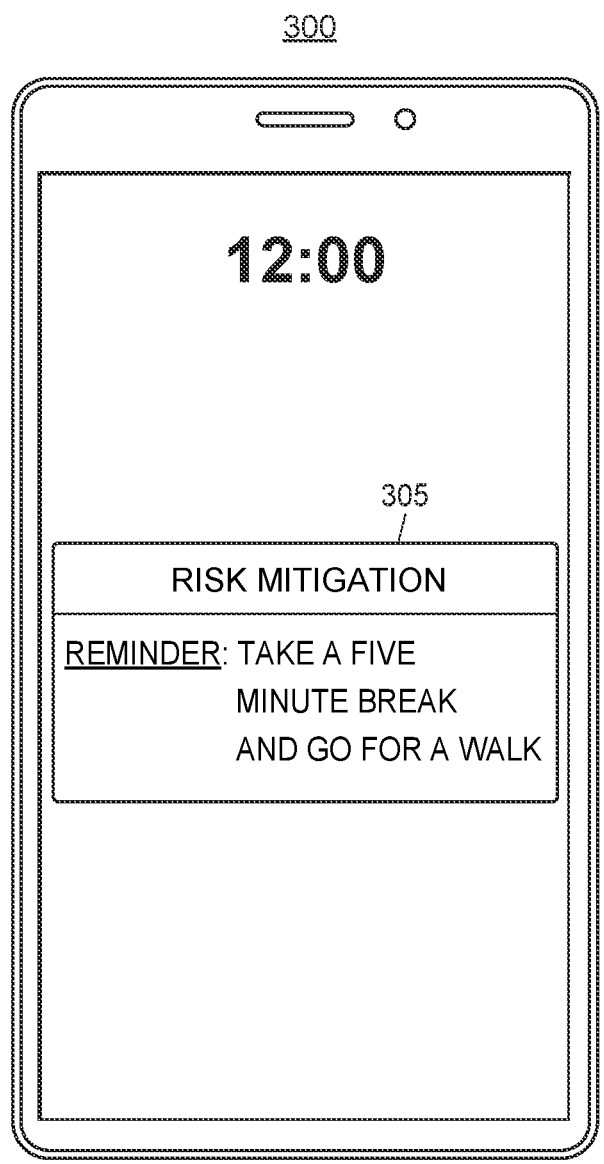
FIG. 3 is an example user interface screen displaying an example of a communication as part of a risk mitigation strategy.

FIG. 3 illustrates an example user-interface 300 displaying a communication which is part of a risk mitigation strategy. As described above, the risk mitigation strategy includes a series of communications intended to be transmitted to a user corresponding to a risk score. The communications may be in the form of text, video, interactive displays, etc. In the example user-interface 300, the communication 305 is in the form a text message reminding a user to take a short break. The risk mitigation strategy is intended to provide guidance and recommendations for a user to improve their quality of life and to lower their exposure to various risks. The example communication 305 may be part of a risk mitigation strategy for a user that has a sedentary lifestyle and has high risk scores related to that lifestyle.

In other embodiments, the communications can include driving tips and/or navigations directions for users that have high risks of accidents associated with driving. For example, a user may regularly drive on a route that has a lot a traffic and has a relatively high number of collisions. The communications may inform the user of another route that is has less traffic and fewer collisions.

In other embodiments, the communications may include links to download rideshare apps or contain phone numbers for local taxi services for users that spend a relatively large amount of time at bars or similar establishments. In other embodiments, the communications may include advertisements or links to safety equipment or other products for users that have a high risk of injury or accident. Further, the communications may include videos detailing specific workouts or other exercise related communications for users with a high risk score relating to heart or health related ailments.

The above examples of communications are not intended to be limiting, and risk mitigation strategies can include any number of communications to be sent periodically to a user to help them develop habits to help mitigate risk. As described above, the risk mitigation strategies can be analyzed for effectiveness by comparing data relating to users' health and insurance data to their risk scores. Risk mitigation strategies that correspond to users that have a lower rate of incident as projected by their risk scores can be considered effective. Similarly, if a portion of users belonging to a particular test group have a lower rate of incident than other members of their test group, then communications sent to the portion of users will be considered to be more effective. The effective communications will accordingly be weighted higher and thus selected more often for future risk mitigation strategies.

Several example methods that can be implemented in the system of FIG. 1A are discussed next with reference to FIG. 4 and FIG. 6.

Figure 4:
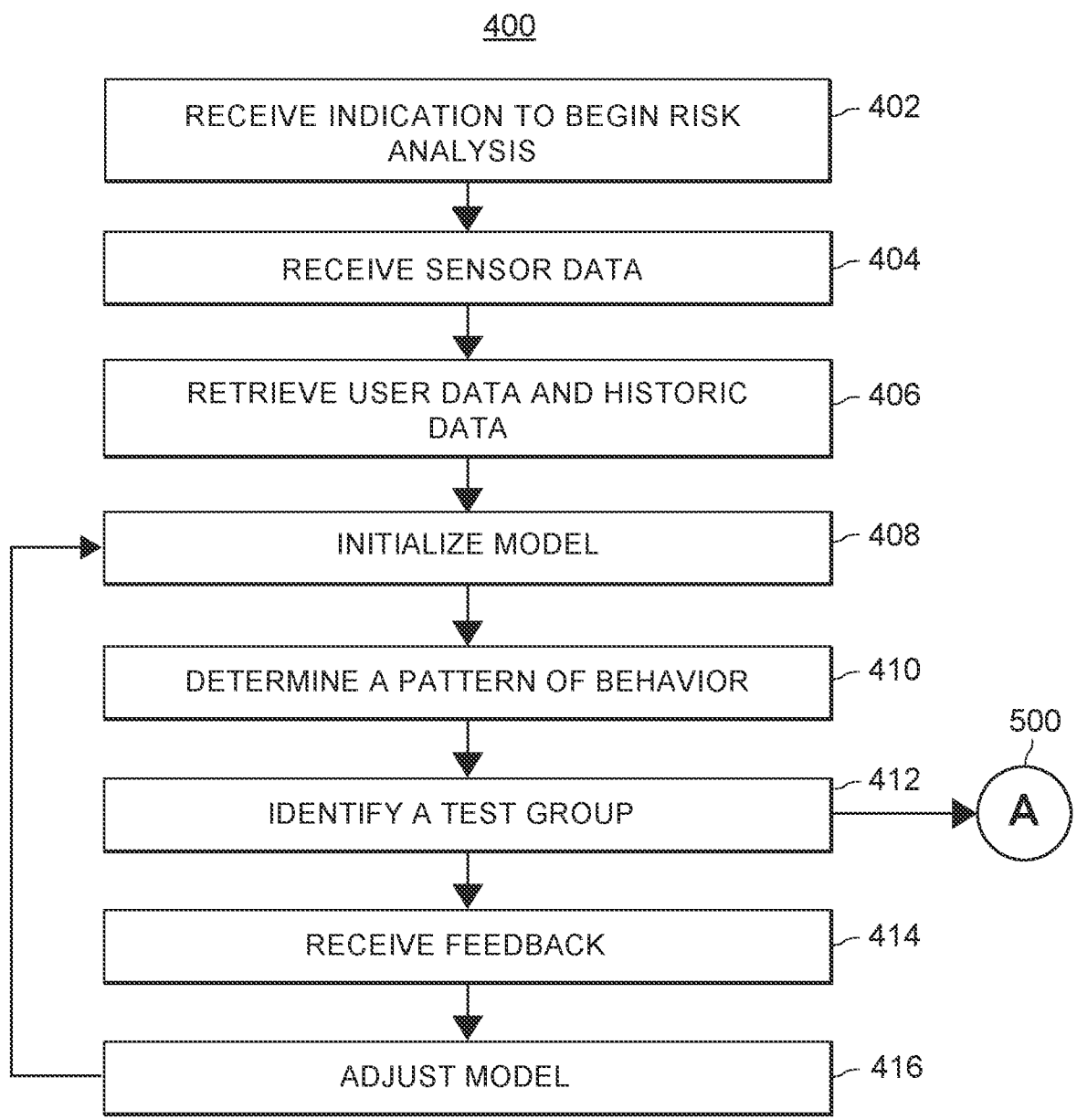
FIG. 4 is a flow diagram of an example method for determining a test group for a user using a machine learning model, which can be implemented in the system of FIG. 1A.

FIG. 4 is a flow diagram of an example method for determining a test group for a user using a machine learning model, which can be implemented in the system of FIG. 1A. Referring first to FIG. 4, an example method 400 for identifying test groups using a machine learning model can be implemented as a set of instructions stored on a computer-readable memory and executable by one or more processors on the server 104. For convenience, the method 400 is discussed below with reference to the risk module 121, grouping engine 122, risk analyzer 124, risk mitigation engine 126 of FIG. 1A, and the corresponding test group model 123, risk analyzer model 125 and the mitigation model 127 of FIG. 1B collectively referred to as the risk system.

At block 402, the risk system may receive an indication to begin a risk analysis. In an example embodiment, the system may receive an indication through a user-interface of a client device to being tracking sensor data on one or more client device in order to perform the risk analysis to determine a risk score and identify risk mitigation strategies. In another embodiment, an insurance provider may initialize the risk analysis for a plurality of customers that have consented to sharing their sensor data.

The risk system receives sensor data at block 404. As described above, the sensor data may be from one or more client devices corresponding to a user. In another embodiment, the risk system may receive a large collect of sensor data corresponding to a plurality of users, where the sensor data is anonymously attributable to one of the plurality of users. The sensor data may include any of GPS data, accelerometer data, gyroscope data, heart rate data, compass data, etc.

At block 406 the risk system retrieves user data and historic data from one or more databases. In an embodiment, the risk system may retrieve any data from any privately or publicly accessible databases containing relevant data for performing risk analysis and, more particularly, for determining test groups. The retrieved data can include demographic data, sensor data, insurance data, weather data, accident data, etc.

At block 408 the system may initialize a test group machine learning model for determining test groups. In an embodiment, the machine learning model may be initialized using a set of initial test groups related to certain patterns of behavior. As described in detail below, the initial model can be improved through an iterative process where feedback and new data is constantly applied to inform and adjust the model. Further, as the risk system retrieves and receives larger sets of data, the risk system may identify a larger number of test groups that are smaller and more precise by applying clustering algorithms to the large data sets.

At block 410 the risk system may determine a pattern of behavior based at least in part upon sensor data and the retrieved data. As described above, the pattern of behavior generally indicates details beyond typical demographic data. In particular, the pattern of behavior indicates not only "where" but also "how" users spend their time. The patterns of behavior may provide a more accurate representation of a risk profile of a user as opposed to simple demographic data. For example, two individuals that share similar demographics (e.g., age, weight, height, race, location, occupation, etc.) may have entirely different lifestyles which may indicate that they have different exposure to risk. For example, the first individual may be sedentary at work and spend most of the time at their desk, while the second individual spends more time walking around the office. Further, the second user may spend thirty minutes exercising everyday while the first user does not. Previous systems would likely not consider these factors and the two individuals would likely be considered to have a similar risk profile in previous risk analysis systems. In contrast, the risk system of the current disclosure would differentiate the two individuals and place them each in separate test groups, as their patterns of behavior (e.g., lifestyle) are not similar.

At block 412 the risk system may determine a test group based at least in part upon the pattern of behavior using the test group machine learning model. As noted above, the test groups may be of any suitable size. The risk system may determine test groups heuristically and/or through clustering algorithms, classification or any other known techniques for analyzing large data sets. As more data and feedback are received, and as the model is adjusted (e.g., see blocks 414 and 416), the model may more precisely identify test groups and further identify patterns of behavior that are more relevant for a risk analysis. For example, certain aspects in the patterns of behavior may be more strongly correlated to risk, and those aspects will be weighted more heavily and factor more heavily in identifying test groups. The test groups may then be used to determine risk scores (e.g., method 500).

At block 414, the risk system may receive feedback. The feedback may be in the form of updated information corresponding to the users of the test group. For example, the users of the test group may be involved in incidents corresponding to risk such as an accident, an illness, an injury, a hospital stay, an insurance claim, etc. The risk system may analyze the test group to determine if the users in the group were correctly grouped together.

At block 416 the risk system may adjust the model such that future test groups can reflect the feedback and contain users that are correctly grouped together. In some embodiments the feedback may be used to create new test groups or the manage existing test groups.

Figure 5:
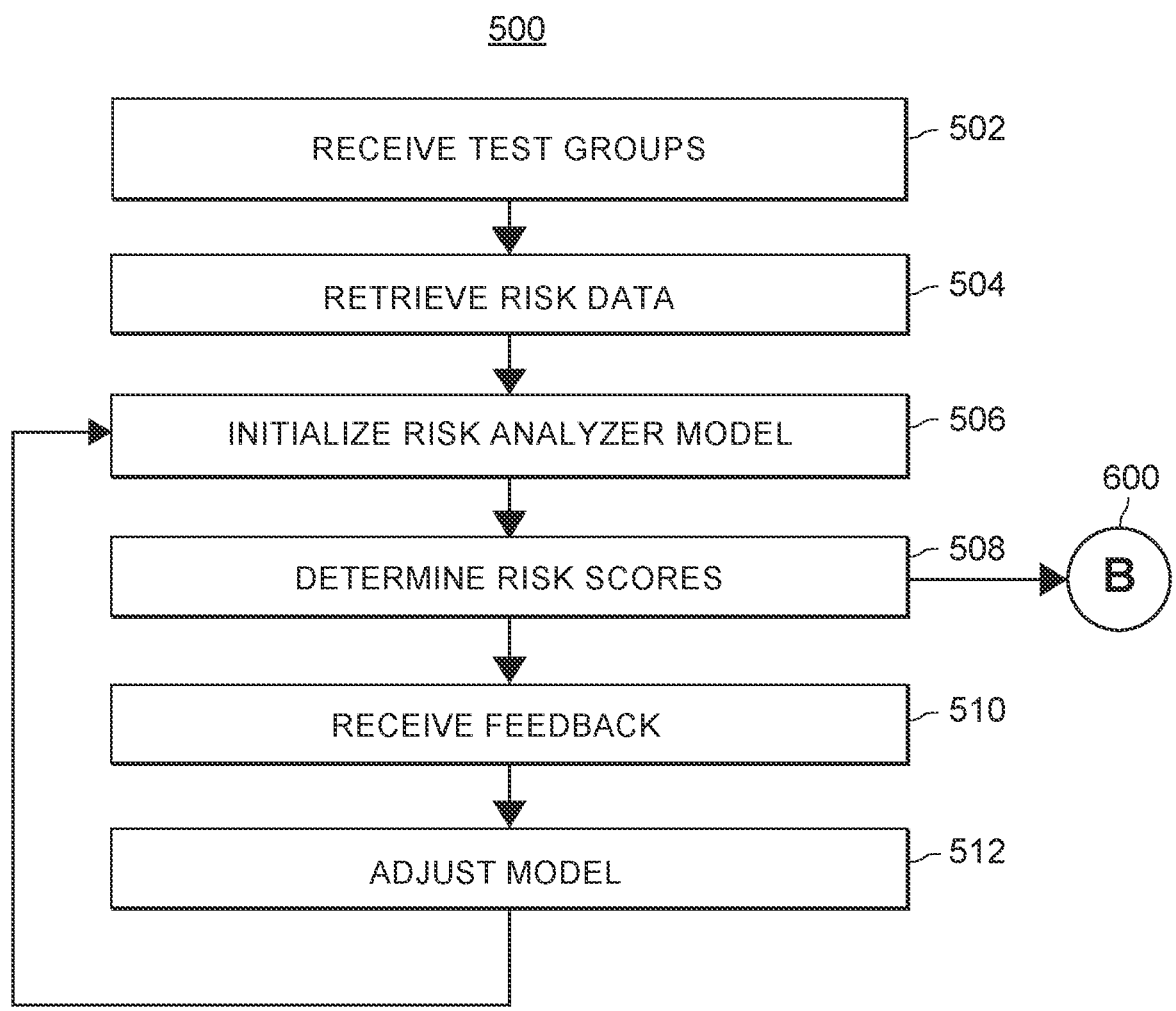
FIG. 5 is a flow diagram of an example method for determining a risk score for a user using a machine learning model, which can be implemented in the system of FIG. 1A.

FIG. 5 is an example method 500 for analyzing risk of a test group to determine a risk score using a machine learning model. The method 500 can be implemented as a set of instructions stored on a computer-readable memory and executable by one or more processors on the server 104. For convenience, the method 500 is discussed below with reference to the risk module 121, grouping engine 122, risk analyzer 124, risk mitigation engine 126 of FIG. 1A, and the corresponding test group model 123, risk analyzer model 125 and the mitigation model 127 of FIG. 1B collectively referred to as the risk system.

At block 502, the risk system may receive test groups, such as the test groups identified at block 412 of method 400.

At block 504 the risk system retrieves risk data, user data and historic data from one or more databases. In an embodiment, the risk system may retrieve any data from any privately or publicly accessible databases containing relevant data for determining risk scores. The retrieved data can include demographic data, sensor data, insurance data, weather data, accident data, etc.

At block 506 the system may initialize a risk analyzer machine learning model for determining risk scores. In an embodiment, the risk analyzer model may be initialized using a set of risk algorithms based at least in part upon data related to the patterns of behavior of the test group. As described in detail below, the initial model can be improved through an iterative process where feedback and new data is constantly applied to inform and adjust the model. Further, as the risk system retrieves and receives larger sets of data, the risk system may refine the algorithms in order to process the data in a manner that leads to more accurate risk scores.

At block 508 the risk system may determine risk scores based at least in part upon the test groups and the retrieved data using a risk analyzer machine learning model. The risk system may determine risk scores heuristically and/or through clustering algorithms, classification or any other known techniques for analyzing large data sets. In an example embodiment, the risk system may determine a set or risk scores, each of the risk scores indicative of a different type of risk. For example, the risk system may determine a composite risk score as well as risk scores related to mental health risks, accident risk, injury risk, risk of exposure, risk of death, risk of illness, risk of crime, etc. The risk system may determine a risk score corresponding to any relevant category for insurance or medical purposes. In an embodiment, each of the users of the test group may be given the same risk scores. In another embodiment, each of the users of the test group may be given the same risk score, where each individual user's risk score is further personalized based at least in part upon their specific pattern of behavior. The risk scores may then be used to determine risk mitigation strategies (e.g., method 600).

At block 510, the risk system may receive feedback. The feedback may be in the form of updated information corresponding to the users of the test group. For example, the users of the test group may be involved in incidents corresponding to risk such as an accident, an illness, an injury, a hospital stay, an insurance claim, etc. The risk system may analyze the risk scores in view of the feedback to determine if the risk scores were accurate.

At block 512 the risk system may adjust the model such that risk scores for test groups are adjusted to accurately reflect the feedback. In some embodiments the feedback may be used to create new test groups or the manage existing test groups.

Figure 6:
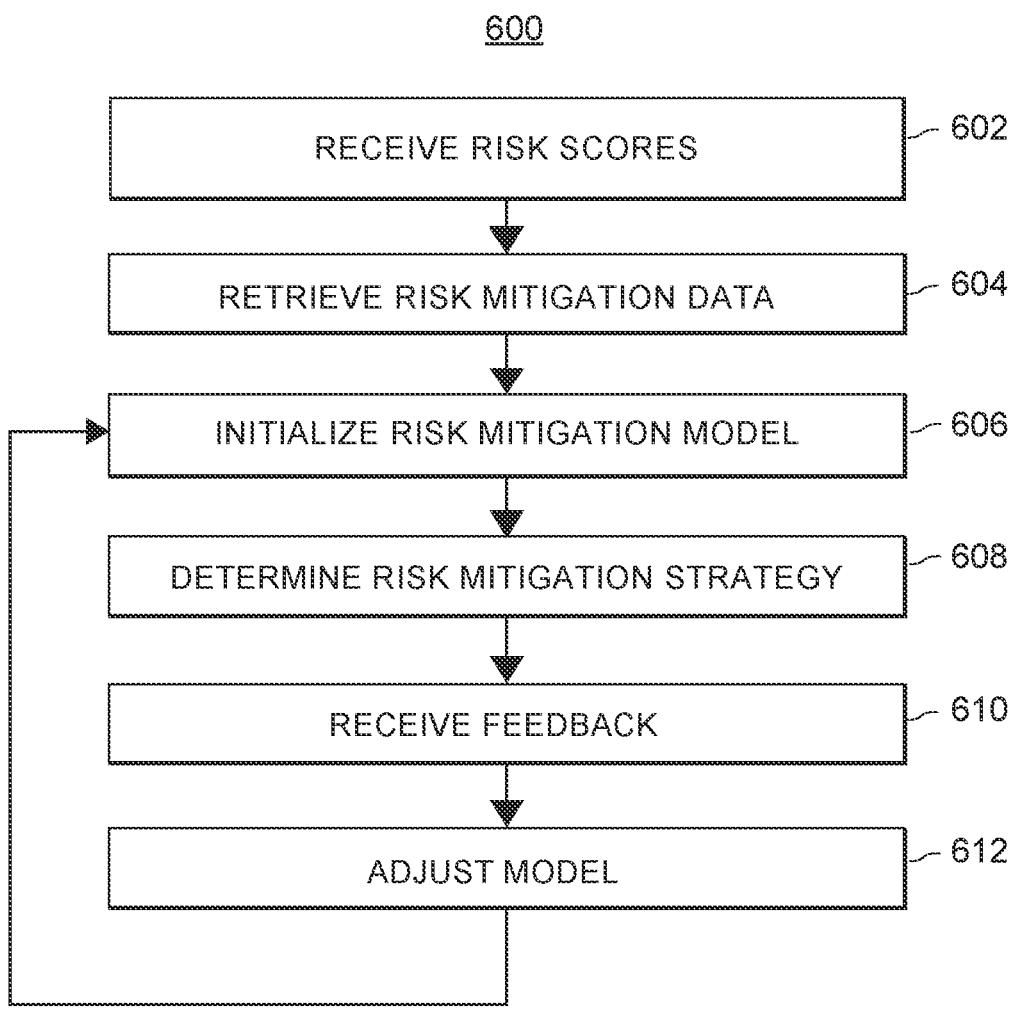
FIG. 6 is a flow diagram of an example method for providing risk mitigation strategy using a machine learning model, which can be implemented in the system of FIG. 1A.

FIG. 6 is an example method 600 for analyzing risk scores to determine a risk mitigation strategy using a machine learning model. The method 600 can be implemented as a set of instructions stored on a computer-readable memory and executable by one or more processors on the server 104. For convenience, the method 600 is discussed below with reference to the risk module 121, grouping engine 122, risk analyzer 124, risk mitigation engine 126 of FIG. 1A, and the corresponding test group model 123, risk analyzer model 125 and the mitigation model 127 of FIG. 1B collectively referred to as the risk system.

At block 602, the risk system may receive risk scores, such as the risk scores identified at block 508 of method 500.

At block 604 the risk system retrieves risk mitigation data, user data and historic data from one or more databases. In an embodiment, the risk system may retrieve any data from any privately or publicly accessible databases containing relevant data for determining risk mitigation strategies. The retrieved data can include demographic data, sensor data, insurance data, weather data, accident data, etc.

At block 606 the system may initialize a risk mitigation machine learning model for determining risk mitigation strategies. In an embodiment, the risk mitigation model may be initialized using a set of communications based at least in part upon risk scores, where each communication corresponds to a risk score range. As described in detail below, the initial model can be improved through an iterative process where feedback and new data is constantly applied to inform and adjust the mitigation model. Further, as the risk system retrieves and receives larger sets of data, the risk system may determine that certain communications have a higher success rate or correspond to users having a lower rate of incident compared to their risk score. The risk system will weight successful communications higher and subsequently select successful communications with greater frequency for further risk mitigation strategies.

At block 608 the risk system may determine risk mitigation strategies based at least in part upon the risk scores and the retrieved data using a risk mitigation machine learning model. The risk system may determine risk mitigation strategies heuristically and/or through clustering algorithms, classification or any other known techniques for analyzing large data sets. In an example embodiment, the risk system may determine a risk mitigation strategy including a set of communications to be transmitted to a user corresponding to the risk scores. The communications of the risk mitigations strategies may include texts, videos, links, navigation directions, etc., as discussed above with respect to FIG. 3. In some embodiments, the risk system may track the risk mitigation strategy until completion and, upon completion, retrieve new data and sensor data and determine a new risk score for the user (e.g., including identifying a new test group, if applicable).

At block 610, the risk system may receive feedback. The feedback may be in the form of updated information corresponding to the users of the test group, and specifically those that have received communications as part of a risk mitigation strategy. For example, the users of the test group may be involved in incidents corresponding to risk such as an accident, an illness, an injury, a hospital stay, an insurance claim, etc. The risk system may analyze the risk mitigation strategy in view of the risk scores and the feedback to determine if the risk mitigation strategy decreased the risk of the user. For example, if users of a test group experienced lower incidents compared to their determined risk score, then the risk mitigation strategy may be considered successful, and any communications included in the risk mitigation strategy may be determined to be effective (e.g., and subsequently selected at a higher rate in future risk mitigation strategies).

At block 612 the risk system may adjust the risk mitigation model such that future risk mitigation strategies can reflect the feedback.

EXAMPLES OF ADDITIONAL CONSIDERATIONS

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing needs that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter of the present disclosure.

Additionally, certain embodiments are described herein as including logic or a number of components, modules, or mechanisms. Modules may constitute either software modules (e.g., code stored on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term hardware should be understood to encompass a tangible entity, be that an entity that is physically constructed, permanently configured (e.g., hardwired), or temporarily configured (e.g., programmed) to operate in a certain manner or to perform certain operations described herein. As used herein "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly be configured on a processor, for example, to constitute a particular hardware module at one instance of time and to constitute a different hardware module at a different instance of time.

Hardware modules can provide information to, and receive information from, other hardware. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The methods 400, 500, and 600 may include one or more function blocks, modules, individual functions or routines in the form of tangible computer-executable instructions that are stored in a non-transitory computer-readable storage medium and executed using a processor of a computing device (e.g., a server, a personal computer, a smart phone, a tablet computer, a smart watch, a mobile computing device, or other personal computing device, as described herein). The methods 400, 500, and 600 may be included as part of any backend server (e.g., a data server, a risk server, or any other type of server computing device, as described herein), portable device modules of the example environment, for example, or as part of a module that is external to such an environment. Though the figures may be described with reference to the other figures for ease of explanation, the methods 400, 500, and 600 can be utilized with other objects and user interfaces. Furthermore, although the explanation above may describe steps of the methods 400, 500, and 600 being performed by specific devices (such as a client computing device 102, and a server 104), this is done for illustration purposes only.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as an SaaS. For example, as indicated above, at least some of the operations may be performed by a group of computers (e.g., as examples of machines including processors), these operations being accessible via a network (e.g., the Internet) and via one or more appropriate interfaces (e.g., APIs).

Still further, the figures depict some embodiments of the example environment for purposes of illustration only. One skilled in the art will readily recognize from the following discussion that alternative embodiments of the structures and methods illustrated herein may be employed without departing from the principles described herein.

Upon reading this disclosure, those of skill in the art will appreciate still additional alternative structural and functional designs for providing risk analysis and mitigation through the disclosed principles herein. Thus, while particular embodiments and applications have been illustrated and described, it is to be understood that the disclosed embodiments are not limited to the precise construction and components disclosed herein.

Although specific embodiments of the present disclosure have been described, it will be understood by those of skill in the art that there are other embodiments that are equivalent to the described embodiments. Accordingly, it is to be understood that the present disclosure is not to be limited by the specific illustrated embodiments.

What is claimed:

1. A computer-implemented method for providing risk analysis and mitigation, the method comprising:
   receiving, by the one or more processors, sensor data indicative of one or more physical measurements corresponding to a user;
   retrieving, from one or more databases communicatively coupled to the one or more processors, demographic data corresponding to the user;
   analyzing, by the one or more processors, the sensor data and the demographic data to determine a pattern of behavior of the user;
   selecting a test group corresponding to the user based at least in part upon the pattern of behavior; and
   determining, by the one or more processors, a risk score of the user based at least in part upon the test group;
   wherein the test group includes a plurality of subjects, each subject of the plurality of subjects corresponds to the pattern of behavior of the user.

2. The computer-implemented method of claim 1, further comprising:
   generating, by the one or more processors, a risk mitigation strategy based at least in part upon the risk score;
   wherein the risk mitigation strategy includes a series of communications to be sent to the user periodically,
   wherein each communication of the series of communications is selected from a plurality of communications.

3. The computer-implemented method of claim 2, further comprising:
   upon completing the generating the risk mitigation strategy, determining, a new risk score for the user.

4. The computer-implemented method of claim 2, further comprising:
   training, by the one or more processors, a mitigation machine learning model configured to output the risk mitigation strategy,
   wherein the training the mitigation machine learning model includes applying mitigation training data that includes (i) the plurality of communications, (ii) the risk score, and (iii) mitigation initialization data.

5. The computer-implemented method of claim 1, wherein the sensor data include one of: (i) GPS data, (ii) accelerometer data, (iii) raw gyroscope data, and (iv) heart-rate data.

6. The computer-implemented method of claim 1, wherein the sensor data is collected from one or more devices corresponding to the user.

7. The computer-implemented method of claim 1, where the risk score comprises one of (i) illness, (ii) accident, (iii) injury, (iv) death, (v) mental health, and (vi) exposure.

8. The computer-implemented method of claim 1, further comprising:
   receiving, periodically by the one or more processors, feedback corresponding to the test group,
   wherein the feedback includes insurance claims data and health data.

9. The computer-implemented method of claim 8, further comprising:
   training, by the one or more processors, a test group machine learning model configured to output the test group based at least in part upon the pattern of behavior,
   wherein training the test group machine learning model includes applying test group training data that include (i) test group initialization data (ii) a plurality of sensor data corresponding to the plurality of subjects (iii) a plurality of demographic data corresponding to the plurality of subjects, and (iv) the feedback.

10. The computer-implemented method of claim 9, further comprising:
    training, by the one or more processors, a risk analyzer machine learning model configured to output the risk score based at least in part upon the test group,
    wherein the training the risk analyzer machine learning model includes applying training data that include (i) a plurality of test groups, (ii) risk initialization data, and (iii) the feedback.

11. A system for providing risk analysis and mitigation, the system compromising:
    a server; and
    a risk module configured to execute on one or more processors at least partially on the server, the risk module configured to:
    receive, sensor data indicative of one or more physical measurements corresponding to a user;
    retrieve, from one or more databases communicatively coupled to the server, demographic data corresponding to the user;
    analyze the sensor data and the demographic data to determine a pattern of behavior of the user;
    select a test group corresponding to the user based at least in part upon the pattern of behavior; and
    determine a risk score of the user based at least in part upon the test group;
    wherein the test group includes a plurality of subjects, each subject of the plurality of subjects corresponds to the pattern of behavior of the user.

12. The system of claim 11, wherein the risk module is further configured to:
    generate a risk mitigation strategy based at least in part upon the risk score,
    wherein the risk mitigation strategy includes a series of communications to be sent to the user periodically,
    wherein each communication of the series of communication is selected from a plurality of communications.

13. The system of claim 12, wherein the risk module is further configured to:
    upon completion of the generation of the risk mitigation strategy, determine a new risk score for the user.

14. The system of claim 12, wherein the risk module is further configured to:
    train a mitigation machine learning model configured to output the risk mitigation strategy,
    wherein to train the mitigation machine learning model includes to apply mitigation training data that include (i) the plurality of communications, (ii) the risk score, and (iii) mitigation initialization data.

15. The system of claim 11, wherein the sensor data include one of: (i) GPS data, (ii) accelerometer data, (iii) raw gyroscope data, and (iv) heartrate data.

16. The system of claim 11, wherein the risk module is further configured to:
    receive, periodically, feedback corresponding to the test group,
    wherein the feedback includes insurance claims data and health data.

17. The system of claim 16, wherein the risk module is further configured to:
    train a test group machine learning model configured to output the test group based at least in part upon the pattern of behavior,
    wherein to train the mitigation machine learning model includes to apply test group training data that include (i) test group initialization data (ii) a plurality of sensor data corresponding to the plurality of subjects (iii) a plurality of demographic data corresponding to the plurality of subjects, and (iv) the feedback.

18. The system of claim 17, wherein the risk module is further configured to:
    train, by the one or more processors, a risk analyzer machine learning model configured to output the risk score based at least in part upon the test group,
    wherein to train the mitigation machine learning model includes to apply training data that include (i) a plurality of test groups, (ii) risk initialization data, and (iii) the feedback.

19. A tangible computer-readable medium including non-transitory computer readable instructions stored thereon for providing risk analysis and mitigation, the instructions when executed causes one or more processors to:
    implement a risk module configured to execute on one or more processors, the risk module configured to:
        receive, sensor data indicative of one or more physical measurements corresponding to a user;
        retrieve, from one or more databases communicatively coupled to a server, demographic data corresponding to the user;
        analyze the sensor data and the demographic data to determine a pattern of behavior of the user;
        select a test group corresponding to the user based at least in part upon the pattern of behavior; and
        determine a risk score of the user based at least in part upon the test group;
    wherein the test group includes a plurality of subjects, each subject of the plurality of subjects corresponds to the pattern of behavior of the user.

20. The tangible computer-readable medium of claim 19, wherein the risk module is further configured to:
    generate a risk mitigation strategy based at least in part upon the risk score,
    wherein the risk mitigation strategy includes a series of communications to be sent to the user periodically,
    wherein each communication of the series of communication is selected from a plurality of communications.

* * * * *